US006465455B1

(12) United States Patent
Brown et al.

(10) Patent No.: US 6,465,455 B1
(45) Date of Patent: Oct. 15, 2002

(54) BENZAMIDE DERIVATIVES FOR THE TREATMENT OF DISEASES MEDIATED BY CYTOKINES

(75) Inventors: Dearg S Brown; George R Brown, both of Macclesfield (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/674,428

(22) PCT Filed: May 11, 1999

(86) PCT No.: PCT/GB99/01491

§ 371 (c)(1), (2), (4) Date: Nov. 1, 2000

(87) PCT Pub. No.: WO99/59960

PCT Pub. Date: Nov. 25, 1999

(30) Foreign Application Priority Data

| | | |
|---|---|---|
| May 15, 1998 | (GB) | 9810356 |
| Mar. 17, 1999 | (GB) | 9905970 |

(51) Int. Cl.[7] .................... C07C 235/56; A61K 31/165; A61P 29/00; A61P 37/02

(52) U.S. Cl. .............................. 514/231.2; 514/252.12; 514/315; 514/617; 514/619; 564/155; 544/106; 544/194; 544/358; 548/567

(58) Field of Search .......................... 564/155; 514/617, 514/619, 315, 252.12, 231.2; 544/106, 358, 194; 548/567; 546/194

(56) References Cited

U.S. PATENT DOCUMENTS

| | | | | |
|---|---|---|---|---|
| 1,903,899 A | 4/1933 | Laska et al. | 564/155 |
| 1,909,960 A | 5/1933 | Hitch | 564/155 |
| 4,524,168 A | 6/1985 | Wick | 524/190 |
| 4,749,729 A | 6/1988 | Kohli et al. | 523/468 |

FOREIGN PATENT DOCUMENTS

| | | |
|---|---|---|
| EP | 0 849 256 | 6/1998 |
| GB | 28 12 252 | 10/1979 |
| WO | WO 93/04170 | 3/1993 |
| WO | WO 97/05878 | 2/1997 |
| WO | WO 97/32853 | 9/1997 |
| WO | WO 98/06715 | 2/1998 |
| WO | WO 98/22103 | 5/1998 |
| WO | WO 99/15164 | 4/1999 |
| WO | WO 99/59959 | 11/1999 |
| WO | WO 99/59960 | 11/1999 |
| WO | WO 00/07980 | 2/2000 |
| WO | WO 00/07991 | 2/2000 |
| WO | WO 00/18738 | 4/2000 |
| WO | WO 00/20402 | 4/2000 |
| WO | WO 00/55120 | 9/2000 |
| WO | WO 00/55153 | 9/2000 |
| WO | WO 99/56738 | 9/2000 |
| WO | WO 01/27089 | 4/2001 |

OTHER PUBLICATIONS

Adams et al., "Search for trypanocides. III. Analogs of suramin.", Chemical Abstracts, vol. 51, 1957, cols. 5067 and 5068.

Ando et al., Magn. Reson.Chem. 639–45, 1995, Chemical Abstract: 123:227514, 1995.

Ando et al., "Producing azo lake pigments"; Chemical Abstract, vol. 106, Abstract No. 215574.

Ashton et al., "New Low–Density Lipoprotein Receptor Upregulators Acting via a Novel Mechanism", J. Med. Chem., 1996, vol. 39, pp. 3343–3356.

Ito et al., Photosensitive material containing microencapsulated hydrazine derivatives; Chemical Abstract, vol. 118, Abstract No. 70021.

Lesiak, "New amides of pyrrole–N– and indole–N–caboxylic acids", Chemical Abstracts, No. 126704v, XP–002121335.

Makoto, "Amide and Its Use"; Patent Abstracts of Japan, Abstract No. 09124571, May 13, 1997, also attached: Abstract (Derwent); XP 002086154.

Mühlbach, "Pyrazoles—A Novel Class of Blocking Agents for Isocyanates", Journal of Polymer Science: Part A: Polymer Chemistry, vol. 32, Mar. 1994, pp. 753–765.

Sugawara et al., Kogyo Kaguku Zasshi 72(11)2425–2429, 1969, Chemical Abstract: 72:66514, 1970.

(List continued on next page.)

*Primary Examiner*—Mukund J. Shah
*Assistant Examiner*—Venkataraman Balasubramanian
(74) *Attorney, Agent, or Firm*—Morgan, Lewis & Brockius LLP

(57) ABSTRACT

The invention concerns amide derivatives of Formula (I) wherein: $R^1$ and $R^2$ include hydroxy, $C_{1-6}$alkoxy, mercapto, $C_{1-6}$akylthio, amino and heterocyclyl; m and p are independently 0–3; $R^3$ is halo, cyano or $C_{1-6}$alkoxy; q is 0–4; and $R^4$ is aryl or cycloalkyl wherein $R^4$ is optionally substituted with up to 3 substituents having any value defined for each $R^1$ group; or a pharmaceutically-acceptable salt or in-vivo-cleavable ester thereof; processes for their preparation, pharmaceutical compositions containing them and their use in the treatment of diseases or medical conditions mediated by cytokines.

(I)

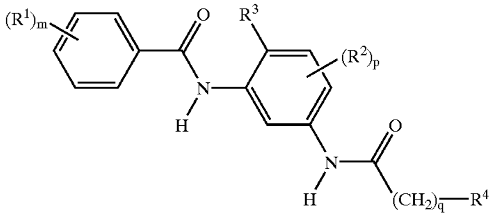

10 Claims, No Drawings

OTHER PUBLICATIONS

Wang et al., "Low–valent Titanium–induced Reactions of Substituted Nitrobenzenes", J. Chem. Research, 1998, pp. 182–183.

Hamuro et al., "Novel Folding Patterns in a Family of Oligoanthranilamides . . . Secondary Structures", J. Amer. Chem. Soc., 1997, pp. 10587–10593.

Chemical Abstract No. 12932a, vol. 51, 1957.

Chemical Abstract No. 12076g, vol. 65, 1966.

Petrova et al., "Determination of the Structure of the Oxidative . . . by Spectroscopic Methods", Journal of Molecular Structure, vol. 142, 1986, pp. 459–462.

Beilstein Reg. No. 3534091.

Beilstein Reg. No. 3483669.

Beilstein Reg. No. 3480574.

Beilstein Reg. No. 3451759.

Beilstein Reg. No. 3166971.

Beilstein Reg. No. 2164595.

Hanson G J: "Inhibitors of p38 kinase" Expert Opinion on Therapeutic Patents, vol. 7, No. 7, Jan. 1, 1997, pp. 729–733, XP002086152 ISSN: 1354–3776 cited in the application.

BENZAMIDE DERIVATIVES FOR THE TREATMENT OF DISEASES MEDIATED BY CYTOKINES

This application is the national phase of international application PCT/GB99/01491 filed May 11, 1999 which designated U.S.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis eczema and dermatitis) and respiratory disease (especially asthma, bronchitis, allergic rhinitis and adult respiratory distress syndrome), and in the production and development of various cardiovascular and cerebrovascular disorders such as congestive heart failure, myocardial infarction. the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis). Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet,* 1994, 344, 1125 and *British Journal of Rheumatology,* 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFa and IL-1. Known inhibitors of p38 kinase have been reviewed by G. J. Hanson in *Expert Opinions on Therapeutic Patents,* 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

It is known from *J. Med. Chem.,* 1996, 39, 3343–3356, that certain benzamide derivatives can upregulate the expression of the low density lipoprotein (LDL) receptor in human hepatocyte cells. The disclosed compounds included certain N-(2-methoxyphenyl)- and N-(2-halogenophenyl)-benzamide derivatives.

The compound N-(5-benzamido-2-chlorophenyl) benzamide is disclosed in *J. Chem. Res. Synop.,* 1998, 182–183, 886–896 (Chemical Abstracts volume 129, abstract 67538).

According to one aspect of the present invention there is provided a compound of the Formula I Formula I

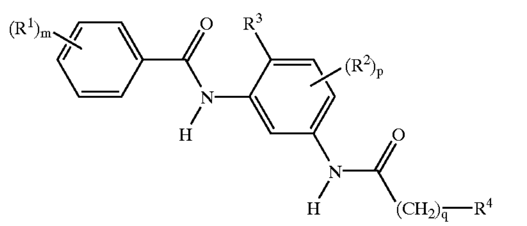

wherein:

$R^1$ and $R^2$, which may be the same or different, are selected from hydroxy, $C_{1-6}$alkoxy, mercapto, $C_{1-6}$alkylthio, amino, $C_{1-6}$alkylamino, di-($C_{1-6}$alkyl)amino, carboxy, $C_{1-6}$alkoxycarbonyl, carbamoyl, $C_{1-6}$alkylcarbamoyl, di-$C_{1-6}$alkylcarbamoyl, $C_{1-6}$alkylsulphinyl, $C_{1-6}$alkylsulphonyl, arylsulphinyl, arylsulphonyl, $C_{1-6}$alkylaminosulphonyl, di-($C_{1-6}$alkyl)aminosulphonyl, nitro, cyano, cyano$C_{1-6}$alkyl, hydroxy$C_{1-6}$alkyl, amino$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, $C_{2-6}$alkenyl, $C_{2-6}$alkynyl, halo, trifluoromethyl, aryl, aryl$C_{1-6}$alkyl, aryl$C_{1-6}$alkoxy, heteroaryl, heteroaryl$C_{1-6}$alkyl, heterocyclyl and heterocycly$C_{1-6}$alkyl;

m and p are independently 0–3, and when m and/or p is 2 or 3 each $R^1$ or $R^2$ group may be the same or different;

$R^3$ is halo, cyano or $C_{1-6}$alkoxy;

q is 0–4; and $R^4$ is aryl or cycloalkyl wherein $R^4$ is optionally substituted with up to 3 substituents having any value defined for each $R^1$ group;

or a pharmaceutically-acceptable salt or in-vivo-cleavable ester thereof;

with the proviso that:

N-[5-(3-cyclohexylpropionylamnino)-2-methoxyphenyl]-4-acetoxybenzamide,

N-[2-bromo-5-(3-cyclohexylpropionylamino)phenyl]-4-hydroxybenzamide,

N-[2-chloro-5-(3-cyclohexylpropionylamino)phenyl]-4-acetoxybenzamide,

N-[2-chloro-5-(3-cyclohexylpropionylamino)phenyl]-4-hydroxybenzamide,

N-[2-fluoro-5-(3-cyclohexylpropionylamino)phenyl]-4-hydroxybenzamide and

N -(5-benzamido-2-chlorophenyl)benzamide are excluded.

"Aryl" in terms such as "aryl", "aryl$C_{1-6}$alkyl", "arylthio", "arylsulphinyl", "arylsulphonyl" and "aryl$C_{1-6}$alkoxy" typically means phenyl or naphthyl, preferably phenyl. "Heteroaryl" in the terms "heteroaryl" and "heteroaryl$C_{1-6}$alkyl" means an aromatic mono- or bicyclic 5–10 membered ring with up to five ring heteroatoms selected from nitrogen, oxygen and sulphur. Examples of 'heteroaryl' include thienyl, pyrrolyl, furyl, imidazolyl, oxazolyl, thiazolyl, pyrazolyl, isoxazolyl, isothiazolyl, pyrazinyl, pyridazinyl, pyrimidinyl, pyridyl, indolyl, benzofuranyl, benzothienyl, benzimidazolyl, benzothiazolyl, quinolyl, isoquinolyl, quinazolinyl, quinoxalinyl and cinnolinyl. "Heterocyclyl" in the terms "heterocyclyl" and "heterocyclyl$C_{1-6}$alkyl" means a non-aromatic mono- or bicyclic 5–10 membered ring with up to five ring hetero atoms selected from nitrogen, oxygen and sulphur. Examples of 'heterocyclyl' include pyrrolinyl, pyrrolidinyl, morpholinyl, piperidinyl, homopiperidinyl, piperazinyl, homopiperazinyl, dihydropyridinyl and dihydropyrimidinyl. "Cycloalkyl" means a non-aromatic mono- or bicyclic 5–10 membered carbon ring. Examples of "cycloalkyl" include cyclopentyl, cyclohexyl, cycloheptyl, bicyclo[2.2.1]heptyl and bicyclo[4.4.0]decyl.

Typical values for other generic groups include: for $C_{1-6}$alkoxy, for example, methoxy and ethoxy, for $C_{1-6}$alkylthio, for example, methylthio and ethylthio, for $C_{1-6}$alkylamino, for example, methylamino and ethylamino, for di-($C_{1-6}$alkyl)amino, for example, dimethylamino, for $C_{1-6}$alkoxycarbonyl, for example, methoxycarbonyl and ethoxycarbonyl, for $C_{1-6}$alkylcarbamoyl, for example, methylcarbamoyl, for di-$C_{1-6}$alkylcarbamoyl, for example, dimethylcarbamoyl, for $C_{1-6}$alkylsulphinyl, for example, methylsulphinyl, for $C_{1-6}$alkylsulphonyl, for example, methylsulphonyl, for $C_{1-6}$alkylaminosulphonyl, for example, methylaminosulphonyl, for di-($C_{1-6}$alkyl) aminosulphonyl, for example, dimethylaminosulphonyl, for cyano$C_{1-6}$alkyl, for example, cyanomethyl, for hydroxy$C_{1-6}$alkyl, for example, hydroxymethyl, for amino$C_{1-6}$alkyl, for example, aminomethyl, for $C_{1-6}$alkanoylamino, for example, formamido and acetamido, for $C_{1-6}$alkoxycarbonylamino, for example, methoxycarbonylamino, for $C_{1-6}$alkanoyl, for example, formyl and acetyl, for $C_{1-6}$alkanoyloxy, for example, acetoxy, for $C_{1-6}$alkyl, for example, methyl, ethyl, isopropyl and tert-butyl, for $C_{2-6}$alkenyl, for example, vinyl and allyl, for $C_{2-6}$alkynyl, for example, ethynyl and 2-propynyl, for halo, for example, fluoro, chloro and bromo, for aryl$C_{1-6}$alkyl, for example, benzyl, and for aryl$C_{1-6}$alkoxy, for example, benzyloxy.

Any ring in $R^1$ or $R^2$ or any ring in a substituent on $R^4$ may be optionally substituted, for example by up to 3 substituents. Suitable substituents include: hydroxy, $C_{1-6}$alkoxy, mercapto, $C_{1-6}$alkylthio, amino, $C_{1-6}$alkylamino, di-($C_{1-6}$alkyl)amino, carboxy, carbamoyl, $C_{1-6}$alkylcarbamoyl, di-$C_{1-6}$alkylcarbamoyl, $C_{1-6}$alkylsulphinyl, $C_{1-6}$alkylsulphonyl, arylsulphinyl, arylsulphonyl, $C_{1-6}$alkylaminosulphonyl, di-($C_{1-6}$alkyl) aminosulphonyl, nitro, cyano, cyano$C_{1-6}$alkyl, hydroxy$C_{1-6}$alkyl, amnino$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, $C_{2-6}$alkenyl, $C_{2-6}$alkynyl, halo and trifluoromethyl.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Preferably $R^1$ is hydroxy, $C_{1-6}$alkoxy, amino, $C_{1-6}$alkylamino, di-($C_{1-6}$alkyl)amino, carboxy, $C_{1-6}$alkoxycarbonyl, carbamoyl, $C_{1-6}$alkylcarbarnoyl, cyano, $C_{1-6}$alkanoylamino, $C_{1-6}$alkanoyl, $C_{1-6}$alkanoyloxy, $C_{1-6}$alkyl, halo, trifluoromethyl or heterocyclyl. Further preferably $R^1$ is amino$C_{1-6}$alkyl.

More preferably $R^1$ is hydroxy, $C_{1-6}$alkoxy, cyano, halo, morpholino or 4-methylpiperazin-1-yl.

Preferably m is 1 or 2.

Conveniently p is 1 and $R^2$ is $C_{1-6}$alkoxy, carboxy, $C_{1-6}$alkoxycarbonyl, $C_{1-6}$alkyl or halo.

Preferably p is 0.

Preferably $R^3$ is halo.

Preferably q is 0, 1 or 2. More preferably q is 0.

Preferably $R^4$ is phenyl, cyclohexyl or cyclopentyl.

More preferably $R^4$ is phenyl.

Preferred substituents on $R^4$ are hydroxy, $C_{1-6}$alkoxy, amino, $C_{1-6}$alkylamino, di-($C_{1-6}$alkyl)amino, carboxy, $C_{1-6}$alkoxycarbonyl, nitro, cyano, $C_{1-6}$alkanoylamino, $C_{1-6}$alkanoyl, $C_{1-6}$alkanoyloxy, $C_{1-6}$alkyl, halo, trifluoromethyl, phenyl, phenyl$C_{1-6}$alkoxy and heterocyclyl.

More preferably substituents on $R^4$ are selected from hydroxy, cyano, dimethylamino, methoxy, ethoxy, fluoro, chloro and morpholino.

Particular novel compounds of the invention include, for example, amide derivatives of the Formula I, or pharnaceutically-acceptable salts thereof, subject to the exclusions defined hereinbefore, wherein:

(a) $R^1$ is hydroxy, $C_{1-6}$alkoxy, amino, $C_{1-6}$alkylamino, di-($C_{1-6}$alkyl)amino, carboxy, $C_{1-6}$alkoxycarbonyl, nitro, cyano, cyano$C_{1-6}$alkyl, hydroxy$C_{1-6}$alkyl, amino$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, halo or trifluoromethyl, and m is 1 or 2; and $R^2$, $R^3$, $R^4$, p and q have any of the meanings defined hereinbefore or in this section relating to particular novel compounds of the invention;

(b) $R^1$ is a non-aromatic saturated 5- or 6-membered heterocyclic ring with one or two heteroatoms selected from nitrogen, oxygen and sulphur, and m is 1 or 2; and $R^2$, $R^3$, $R^4$, p and q have any of the meanings defined hereinbefore or in this section relating to particular novel compounds of the invention;

(c) $R^1$ is a saturated heterocyclic ring selected from pyrrolidinyl, morpholinyl, piperidinyl, piperazinyl and 4-($C_{1-6}$alkyl)piperazinyl, and m is 1 or 2; and $R^2$, $R^3$, $R^4$, p and q have any of the meanings defined hereinbefore or in this section relating to particular novel compounds of the invention;

(d) $R^2$ is hydroxy, $C_{1-6}$alkoxy, amino, $C_{1-6}$alkylamino, di-($C_{1-6}$alkyl)amino, carboxy, $C_{1-6}$alkoxycarbonyl, nitro, cyano, $C_{1-6}$alkyl, halo or trifluoromethyl, and p is 1; and $R^1$, $R^3$, $R^4$, m and q have any of the meanings defined hereinbefore or in this section relating to particular novel compounds of the invention;

(e) p is 0; and $R^1$, $R^3$, $R^4$, m and q have any of the meanings defined hereinbefore or in this section relating to particular novel compounds of the invention;

(f) $R^3$ is halo; and $R^1$, $R^2$, $R^4$, m, p and q have any of the meanings defined hereinbefore or in this section relating to particular novel compounds of the invention;

(g) q is 1, 2, 3 or 4, and $R^4$ is cycloalkyl; and $R^1$, $R^2$, $R^3$, m and p have any of the meanings defined hereinbefore or in this section relating to particular novel compounds of the invention;

(h) q is 0, and $R^4$ is phenyl which is optionally substituted with up to 3 substituents selected from hydroxy, $C_{1-6}$alkoxy, amino, $C_{1-6}$alkylamino, di-($C_{1-6}$alkyl)amino, carboxy, $C_{1-6}$alkoxycarbonyl, nitro, cyano, $C_{1-6}$alkoxycarbonylamino, $C_{1-6}$alkanoyl, $C_{1-6}$alkanoyloxy, $C_{1-6}$alkyl, halo, trifluoromethyl, phenyl, benzyl and benzyloxy; and $R^1$, $R^2$, $R^3$, m and p have any of the meanings defined hereinbefore or in this section relating to particular novel compounds of the invention;

(i) q is 0, and $R^4$ is phenyl which is substituted with 1 or 2 substituents selected from heteroaryl, heteroaryl$C_{1-6}$alkyl, heterocyclyl and heterocyclyl$C_{1-6}$alkyl; and $R^1$, $R^2$, $R^3$, m and p have any of the meanings defined hereinbefore or in this section relating to particular novel compounds of the invention;

(j) q is 0, and $R^4$ is phenyl which is substituted with 1 or 2 heterocyclyl groups comprising a non-aromatic saturated 5- or 6-membered heterocyclic ring with one or two heteroatoms selected from nitrogen, oxygen and sulphur; and $R^1$, $R^2$, $R^3$, m and p have any of the meanings defined hereinbefore or in this section relating to particular novel compounds of the invention; and (k) q is 0, and $R^4$ is phenyl which is substituted with 1 or 2 heterocyclic groups selected from pyrrolidinyl, morpholinyl, piperidinyl, piperazinyl and 4-($C_{1-6}$alkyl)piperazinyl; and $R^1$, $R^2$, $R^3$, m and p have any of the meanings defined hereinbefore or in this section relating to particular novel compounds of the invention.

A preferred compound of the invention is an amide derivative of the Formula I wherein $R^1$ is hydroxy, methoxy, ethoxy, propoxy, isopropoxy, butoxy, amino, methylamino, ethylamino, dimethylamino, diethylamino, carboxy, methoxycarbonyl, ethoxycarbonyl, tert-butoxycarbonyl, cyano, acetamido, acetyl, acetoxy, methyl, ethyl, propyl, isopropyl, butyl, tert-butyl, fluoro, chloro, trifluoromethyl, pyrrolidin-1-yl, morpholino, piperidino, piperazin-1-yl or 4-methylpiperazin-1-yl;

m is 1 or 2;

p is 0;

$R^3$ is fluoro, chloro or bromo;

q is 1, 2 or 3; and $R^4$ is cyclohexyl or cyclopentyl;

or a pharmaceutically-acceptable salt thereof.

A further preferred compound of the invention is an amide derivative of the Formula I wherein $R^1$ is hydroxy, methoxy, ethoxy, propoxy, isopropoxy, butoxy, amino, methylamino, ethylamino, dimethylamino, diethylamino, carboxy, methoxycarbonyl, ethoxycarbonyl, tert-butoxycarbonyl, cyano, acetamido, acetyl, acetoxy, methyl, ethyl, propyl, isopropyl, butyl, tert-butyl, fluoro, chloro, trifluoromethyl, pyrrolidin-1-yl, morpholino, piperidino, piperazin-1-yl or 4-methylpiperazin-1-yl;

m is 1 or 2;

p is 0;

$R^3$ is fluoro, chloro or bromo;

q is 0; and $R^4$ is phenyl which is optionally substituted with 1 or 2 substituents selected from hydroxy, methoxy, ethoxy, propoxy, amino, methylamino, ethylamino, propylamino, dimethylamino, diethylamino, carboxy, methoxycarbonyl, ethoxycarbonyl, nitro, cyano, acetamido, acetyl, acetoxy, methyl, ethyl, fluoro, chloro, bromo, trifluoromethyl, phenyl, benzyloxy, pyrrolidin-1-yl, morpholino, piperidino, piperazin-1-yl and 4-methylpiperazin-1-yl;

or a pharmaceutically-acceptable salt thereof.

A further preferred compound of the invention is an amide derivative of the Formula I wherein $R^1$ is hydroxy, methoxy, ethoxy, cyano, fluoro, chloro, morpholino or 4-methylpiperazin-1-yl;

m is 1 or 2;

p is 0;

$R^3$ is fluoro, chloro or bromo;

q is 0; and $R^4$ is phenyl which is substituted with 1 or 2 substituents selected from hydroxy, methoxy, dimethylamino, methoxycarbonyl, cyano, fluoro, chloro and morpholino;

or a pharmaceutically-acceptable salt thereof.

A further preferred compound of the invention is an amide derivative of the Formula I wherein $R^1$ is hydroxy, methoxy, ethoxy, amino, cyano, acetoxy, fluoro, chloro, morpholino or 4-methylpiperazin-1-yl;

m is 1 or 2;

p is 0;

$R^3$ is fluoro, chloro or bromo;

q is 0; and $R^4$ is phenyl which is unsubstituted or substituted with 1 or 2 substituents selected from hydroxy, methoxy, amino, dimethylamino, methoxycarbonyl, nitro, cyano, fluoro, chloro and morpholino;

or a pharmaceutically-acceptable salt thereof.

Particular preferred compounds of the invention include, for example:

N-[2-chloro-5-(3-cyanobenzamido)phenyl]-3,4-dimethoxybenzamide,

N-[2-chloro-5-(3-dimethylaminobenzamido)phenyl]-3,4-dimethoxybenzamide,

N-[2chloro-5-(4-cyanobenzamido)phenyl]-3,4-dimethoxybenzamide and

N-[2-chloro-5-(4-cyanobenzamido)phenyl]-3-(4-methylpiperazin-1-yl)benzamide;

or the pharmaceutically-acceptable salts thereof.

Further particular preferred compounds of the invention include, for example:

N-(5-benzamido-2-chlorophenyl)-3,4-dimethoxybenzamide,

N-[2-chloro-5-(3-morpholinobenzamido)phenyl]-3,4-dimethoxybenzamide,

N-[5-(4-acetoxybenzamido)-2-chlorophenyl]-4-cyanobenzamide,

N-(5-benzamido-2-chlorophenyl)-2-amino-4-methoxybenzamide and

N-[2-chloro-5-(3-morpholinobenzamido)phenyl]-4-cyanobenzamide;

or the pharmaceutically-acceptable salts thereof.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives. see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32,692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

In order to use a compound of the Formula I or a pharmaceutically acceptable salt or in-vivo-cleavable ester thereof for the therapeutic treatment (including prophylactic treatment) of mammals including humans, it is normally formulated in accordance with standard pharmaceutical practice as a pharmaceutical composition.

According to this aspect of the invention there is provided a pharmaceutical composition which comprises an amide derivative of the Formula I, or a pharmaceutically-acceptable salt or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid: binding agents such as starch; lubricating agents such as magnesium stearate stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calciun carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents. such as sodium carboxymethylcellulose, methylcellulose, hydroxypropylmethylcellulose, sodium alginate, polyvinyl-pyrrolidone, gum tragacanth and gum acacia: dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil. such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore or any of those known compounds excluded from the definition of the compounds of the invention in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof. in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, ischaemic heart disease or psoriasis.

In a further aspect the present invention provides a method of treating rheumatoid arthritis, asthma, irritable bowel disease, multiple sclerosis, AIDS, septic shock, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharnaceutically-acceptable salt or in-vivo-cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase (such as those disclosed in European Patent Applications Nos. 0351194, 0375368. 0375404, 0375452, 037547, 0381375, 0385662, 0385663, 0385679, 0385680).

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan. Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

An amide derivative of the Formula I, or a pharmaceutically-acceptable salt or in-vivo-cleavable ester thereof, may be prepared by any process known to be applicable to the preparation of chemically-related compounds. Suitable processes are illustrated by, for example, those used in *J. Med. Chem.,* 1996, 39, 3343–3356. Such processes, when used to prepare a novel amide derivative of the Formula I are provided as a further feature of the invention and are illustrated by the following representative process variants in which, unless otherwise stated, $R^1$, $R^2$, $R^3$, $R^4$, m, p and q have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

a) A compound of the Formula I, or a pharmaceutically-acceptable salt or in-vivo-cleavable ester thereof, may be prepared by reacting an aniline of the Formula II Formula II

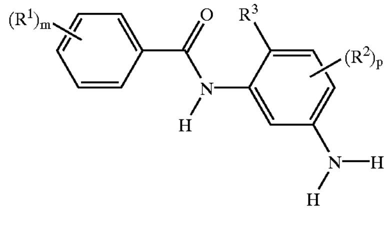

with an acid of the Formula III

Formula III

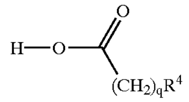

or an activated derivative thereof, under standard amide bond forming conditions, wherein variable groups are as hereinbefore defined and wherein any functional group is protected, if necessary, and:

(i) removing any protecting groups;

(ii) optionally forming a pharmaceutically-acceptable salt or in-vivo-cleavable ester.

A suitable activated derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester. for example an ester formed by the reaction of the acid with a phenol such as pentafluorophenol, with an ester such as pentafluorophenyl trifluoroacetate or with an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl), and $C_{2-6}$alkenyl groups (for example allyl and vinylethyl).

Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The aniline of Formula II may be prepared by reduction of the corresponding nitro compound of Formula IV.

Formula IV

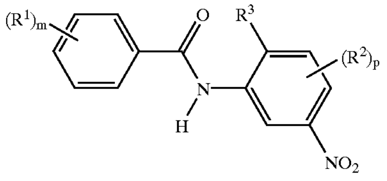

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The compound of Formula IV may be prepared by reaction of an acid of Formula V, or an activated derivative thereof, Formula V

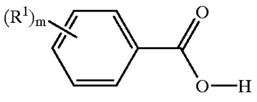

with an aniline for Formula VI under suitable amide bond forming conditions.

Formula VI

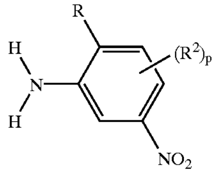

Typical conditions include activating the carboxy group of the compound of Formula V for example by treatment with a halo reagent (for example oxalyl chloride) to form an acyl halide in an organic solvent at ambient temperature, then reacting the activated compound with the aniline of Formula VI. Any functional groups are protected and deprotected as necessary.

(b) A compound of the Formula I, or a pharmaceutically-acceptable salt or in-vivo-cleavable ester thereof, may be prepared by reacting an acid of the Formula V Formula V

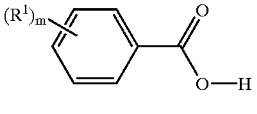

or an activated derivative thereof as defined hereinbefore, with an aniline of the Formula VII Formula VII

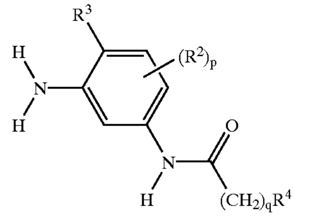

under standard amide bond forming conditions, wherein variable groups are as hereinbefore defined and wherein any functional group is protected, if necessary, and:

(i) removing any protecting groups;

(ii) optionally forming a pharmaceutically-acceptable salt or in-vivo-cleavable ester.

The aniline of Formula VII may be prepared by reduction of the corresponding nitro compound using convention procedures as defined hereinbefore or as illustrated in the Examples.

(c) A compound of the Formula I wherein $R^1$ or a substituent on $R^4$ is an amino group may be prepared by the reduction of a compound of the Formula I wherein $R^1$ or a substituent on $R^4$ is a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric. hydrobromic, sulphuric or acetic acid. The reaction is conveniently carried out in the presence of an organic solvent (preferably a polar protic solvent) and preferably with heating for example to about 60° C. Any functional groups are protected and deprotected as necessary.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of particular test compounds against each of the p38α and p38β isoforms of the enzyme was determined.

Human recombinant MKK6 (GenBank Accesion Number G1209672) was isolated from Image clone 45578 (*Genomics,* 1996, 33, 151) and utilised to produce protein in the form of a GST fusion protein in a pGEX vector using analogous procedures to those disclosed by J. Han et al., *Journal of Biological Chemistry,* 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J.Han et al., *Biochimica et Biophyhsica Acta,* 1995, 1265, 224–227 and Y. Jiang et al., *Journal of Biological Chemistry,* 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM $Mg(OCOCH_3)_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)) was then added followed by 'Labelled ATP' [10 μl; comprising 50 μM ATP, 0.1 $\mu Ci^{33}P$ ATP (Amersham International cat. no. BF1000) and 50 mM $Mg(OCOCH_3)_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow $IC_{50}$ values to be determined.

In vitro Cell-based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs ($2.4 \times 10^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5% $CO_2$/95% air) incubator (Falcon 3072 ; 96 well flat-bottom tissue culture plates). 20 μl lipopolysaccharide [LPS *E.Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac. (*1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology,* vol 2 by Frederick M. Ausbel et al., John Wiley and Sons Inc.).

% inhibition=(*LPS* alone−medium alone)−(test concentration−medium alone)×100 (*LPS* alone−medium alone)

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin. 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology,* vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex vivo/In vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route. for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

% inhibition of TNFα=Mean TNFα (Controls)−Mean TNFα (Treated)×100 Mean TNFα (Controls)

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.,* 146, 857.
2. Williams, R. O. et al., (1992) *Proc. Natl. Acad. Sci.,* 89,9784.
3. Williams. R. O. et al., (1995) *Immunology,* 84, 433.
4 Badger, M. B. et al., (1996) *The Journal of Pharmacology and Experimental Therapeutics,* 279, 1453–1461.

Although the pharmacological properties of the compounds of the Formula I vary with structural change as expected, in general a compound of the Formula I gives over 30% inhibition in the PBMC test at concentrations up to 50 μM. No physiologically unacceptable toxicity was observed at the effective dose for compounds tested of the present invention.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:

DMF N,N-dimethylformamide
HPLC high pressure liquid chromatograph
DMSO dimethylsulphoxide

EXAMPLE 1

N-[2-chloro-5-(3-dimethylaminobenzamido)phenyl]-3,4-dimethoxybenzamide

Oxalyl chloride (0.11 ml) was added dropwise to a stirred suspension of 3-dimethylaminobenzoic acid (0.18 g) in methylene chloride (10 ml) at 20° C. DMF (2 drops) was added and the reaction mixture was stirred for 4 hours. The solvent was evaporated to give a solid. The solid was dissolved in methylene chloride (15 ml) and added dropwise over 5 minutes to a stirred mixture of N-(5-amino-2-chlorophenyl)-3,4-dimethoxybenzamide (0.306 g), triethylamine (0.4 ml), 4-dimethylaminopyridine (0.005 g) and methylene chloride (5 ml). The resultant mixture was stirred at 20° C. for 18 hours. The reaction mixture was washed with water and with a saturated, aqueous sodium bicarbonate solution, dried ($MgSO_4$) and evaporated. The residual oil was purified by column chromatography on silica gel using a 99:1 mixture of methylene chloride and methanol as eluent. There was thus obtained the title compound (0.109 g), m.p. 98–99° C.;

NMR Spectrum: ($CDCl_3$) 3.02 (s, 6H), 3.95 (s, 6H), 6.86 (m, 1H), 6.93 (d, 1H), 7.1 (d, 1H), 7.31 (t, 1H), 7.42 (m, 2H), 7.54 (d, 1H), 7.98 (m, 2H), 8.42 (s, 1H), 8.58 (d, 1H);

Mass Spectrum: $M+H^+$ 454.

The N-(5-amino-2-chlorophenyl)-3,4-dimethoxybenzamide used as a starting material was prepared as follows:

3,4-Dimethoxybenzoyl chloride (2 g) was added to a stirred suspension of 2-chloro-5-nitroaniline (1.72 g) in pyridine (10 ml) at 20° C. The reaction mixture was heated to 100° C. for 1 hour. After cooling to ambient temperature, the reaction mixture was poured into water (100 ml). The resulting precipitate was collected, washed with water and dried. The solid was triturated under methylene chloride (20 ml) to give N-(2-chloro-5-nitrophenyl)-3,4-dimethoxybenzamide (1.2 g), m.p. 231–232° C.; NMR Spectrum: ($DMSOd_6$) 3.82 (s, 6H), 7.08 (d, 1H), 7.62 (m, 1H), 7.82 (d, 1H), 8.08 (m, 1H), 8.54 (d, 1H), 10.07 (m, 1H); Mass Spectrum: $M+H^+$ 337.

The material so obtained (1.12 g) was added portionwise over 10 minutes to a stirred suspension of iron powder (3.0 g) in a mixture of acetic acid (1 ml), water (10 ml) and ethanol (60 ml) which had been warmed to 70–75° C. The resultant mixture was heated to reflux for 1 hour. The mixture was allowed to cool and solid sodium carbonate was added until the mixture was basic (pH=8–9). The mixture was filtered and the solid material was washed with methylene chloride. The filtrate was evaporated and the residue was triturated with ethyl acetate, filtered and the filtrate was evaporated to give the required starting material as a cream-coloured solid, m.p. 146–149° C.; NMR Spectrum: ($CDCl_3$) 3.70 (s, 2H), 3.88 (s, 3H), (s, 3H), 6.31 (m, 1H), 6.74 (d, 1H), 7.06 (d, 1H), 7.37 (m, 1H), 7.42 (d, 1H) 7.92 (d, 1H), 8.30 (s, 1H); Mass Spectrum: $M+H^+$ 307.

EXAMPLE 2

Using an analogous procedure to that described in Example 1, the appropriate benzoyl chloride was reacted with the appropriate aniline to give the compounds described in Table I.

TABLE I

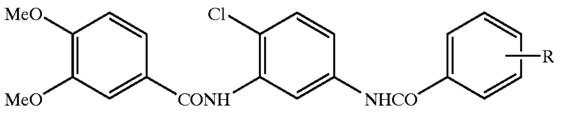

| No. | R | Note | NMR data | Mass |
|---|---|---|---|---|
| 1 | 3-cyano | | 3.81(s, 6H), 7.06(d, 1H), 7.50(d, 1H), 7.56(d, 1H), 7.62 (m, 1H), 7.7(m, 1H), 7.75(d, 1H), 8.03(m, 2H), 8.15 (d, 1H), 8.4(s, 1H), 9.9(s, 1H), 10.56(s, 1H) | M + H 436 |
| 2 | 4-cyano | | 3.82(s, 6H), 7.07(d, 1H), 7.55(d, 1H), 7.58(s, 1H), 7.62(m, 1H), 7.7(m, 1H), 8.01(d, 2H), 8.1(d, 3H), 9.9(s, 1H), 10.62(s, 1H) | M + H 436 |
| 3 | 2-hydroxy | 1. | 3.82(s, 6H), 6.95(m, 2H), 7.05(d, 1H), 7.42 (t, 1H), 7.56(m, 4H), 7.95(d, 1H), 8.03(d, 1H), 9.9(s, 1H), 10.49 (s, 1H) | M + H 427 |
| 4 | 4-methoxy | 2. | | M − H 439 |
| 5 | 2,4-dichloro | 2. | | M + H 479 |
| 6 | 3,4-dichloro | 2. | | M + H 479 |
| 7 | 4-methoxycarbonyl | 2. | | M + H 469 |

Notes
1. The procedure described by Brown et al. in J. Med. Chem., 1985, 28, 143–146 was used.
2. The reaction mixture was purified by HPLC using an increasingly polar gradient mixture of from 5 to 30% methanol in methylene chloride.

EXAMPLE 3

N-[2-bromo-5-(3-dimethylaminobenzamido)phenyl]-3,4-dimethoxybenzamide

Oxalyl chloride (0.24 ml) was added dropwise to a stirred suspension of 3-dimethylaminobenzoic acid (0.36 g) in methylene chloride (15 ml) at 20° C. DMF (2 drops) was added and the reaction mixture was stirred for 4 hours. The solvent was evaporated to give a yellow solid which was dissolved in methylene chloride (20 ml) and added dropwise over 5 minutes to a stirred mixture of N-(5-amino-2-bromophenyl)-3,4-dimethoxybenzamide (0.7 g), triethylamine (0.8 ml), 4-dimethylaminopyridine (0.005 g) and methylene chloride (20 ml) which had been cooled to 5–10° C. The reaction mixture was stirred at ambient temperature for 18 hours. The organic phase was washed with a saturated sodium bicarbonate solution, dried ($MgSO_4$) and evaporated. The residual oil was purified by column chromatography on silica gel using a 49:1 mixture of methylene chloride and methanol as eluent. The solid so obtained was crystallised from a mixture of ethyl acetate and methyl tert-butyl ether to give the title compound (0.564 g), m.p. 184° C.;

NMR Spectrum: ($CDCl_3$) 3.02 (s, 6H), 3.97 (s, 6H), 6.84 (m, 1H), 6.95 (d, 1H), 7.30 (m, 2H), 7.51 (m, 3H), 7.95 (m, 1H), 8.02 (s, 1H), 8.45 (s, 1H), 8.56 (d, 1H), Mass Spectrum: $M+H^+$ 498;

Elemental Analysis: Found C, 55.8; H, 4.5; N, 7.9; $C_{24}H_{24}N_3BrO_4$ $H_2O$ requires C, 55.8; H, 4.9; N, 8.0%.

The N-(5-amino-2-bromophenyl)-3,4-dimethoxybenzamide used as a starting aniline was prepared as follows:

3,4-Dimethoxybenzoyl chloride (2 g) was added to a stirred solution of 2-bromo-5-nitroaniline (2.17 g) at 25° C. The reaction mixture was heated at 100° C. for 5 hours. After cooling, water (25 ml) and 3M hydrochloric acid (100 ml) were added. The resulting solid was filtered off and washed with water (50 ml) and dried. The solid was triturated under diethyl ether to give N-(2-bromo-5-nitrophenyl)-3,4-dimethoxybenzamide (2.01 g ) as a sandy-coloured solid, m.p. 183–184° C.; NMR Spectrum: ($DMSOd_6$) 3.92(s, 6H), 7.08 (d, 1H), 7.56 (d, 1H), 7.65 (m, 1H), 8.0 (s, 2H), 8.4 (s, 1H), 10.09 (s, 1H).

The material so obtained (1.9 g) was added portionwise over 5 minutes to a stirred suspension of iron powder (4.5 g) in a mixture of acetic acid (1.5 ml), water (15 ml) and ethanol (90 ml) which had been warmed to 70–75° C. The mixture was heated to reflux for 0.75 hours. Solid sodium carbonate was added until the mixture was basic (pH=8–9). The hot mixture was filtered and the residue was washed with hot methanol. The filtrates were evaporated and the resultant residue was extracted with hot ethyl acetate (200 ml). The solution was filtered and the filtrate was evaporated to give N-(5-amino-2-bromophenyl)-3,4-dimethoxybenzamide (1.43 g), m.p. 154–155° C.; NMR Spectrum: ($CDCl_3$) 3.88 (s, 2H), 3.94 (s, 3H), 3.96 (s, 3H), 6.38 (m, 1H), 6.93 (d, 1H), 7.25 (d, 1H), 7.46 (m, 1H), 7.55 (d, 1H), 8.02 (d, 1H), 8.38 (s, 1H).

EXAMPLE 4

N-[2-chloro-5-(3-morpholinobenzamido)phenyl]-3,4-dimethoxybenzamide

3-Morpholinobenzoyl chloride (0.15 g) was added to a stirred solution of N-(5-amino-2-chlorophenyl)-3,4-dimethoxybenzamide (0.17 g) in pyridine (3 ml). The reaction mixture was stirred and heated to 115° C. for 18 hours. The mixture was allowed to cool and poured into water. The mixture was extracted with methylene chloride. The organic extract was dried ($MgSO_4$) and evaporated. The resultant solid was azeotroped with toluene and triturated under diethyl ether to give the title compound (0.1 g), m.p. 147.9–148.3° C.;

NMR Spectrum: ($DMSOd_6$) 3.19 (s, 4H), 3.78 (s, 4H), 3.85 (s, 6H), 7.07 (d, 1H), 7.17 (d, 1H), 7.38 (s, 2H), 7.43 (s, 1H), 7.5 (d, 1H), 7.58 (s, 1H), 7.63 (d, 1H), 7.7 (d, 1H), 8.07 (s, 1H), 9.88 (s, 1H), 10.29 (s, 1H);

Mass Spectrum: $M+H^+$ 496;

Elemental Analysis: Found C, 62.2; H, 5.1; N, 8.2; $C_{26}H_{26}N_{30}O_5Cl$ $0.25H_2O$ requires C, 62.4; H, 5.3; N, 8.4%.

The 3-morpholinobenzoyl chloride used as a starting material was prepared as follows:

A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris (dibenzylideneacetone)dipalladium(0) (0.33 g) and toluene (25 ml) was stirred and heated to 90° C. for 18 hours under argon. The reaction mixture was allowed to cool to ambient temperature and extracted with 1M hydrochloric acid. The aqueous phase was basified with concentrated sodium hydroxide solution and extracted with ethyl acetate. The organic phase was dried ($MgSO_4$) and evaporated. The residual oil was purified by column chromatography on silica gel using a 47:3 mixtute of methylene chloride and methanol as eluent. There was thus obtained N-(3-morpholinobenzoyl)morpholine (0.45 g).

A mixture of the material so obtained, 5M sodium hydroxide solution (2.5 ml) and butanol (2 ml) was stirred and heated to 115° C. for 18 hours. The mixture was evaporated and the residue was acidified by the addition of 1M hydrochloric acid solution (12.5 ml). The resultant precipitate was isolated, washed with water and dried to give 3-morpholinobenzoic acid (0.15 g); NMR Spectrum: ($DMSOd_6$) 3.1 (t, 4H), 3.73 (t, 4H), 7.19 (d, 1H), 7.32 (d, 1H), 7.38 (t, 1H), 7.42(s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); Mass Spectrum: $M+H^+$ 222.

EXAMPLE 5

N-[2-chloro-5-(4-cyanobenzamido)phenyl]-4-cyanobenzamide

4-Cyanobenzoyl chloride (0.25 g) was added to a stirred mixture of N-(3-amino-4-chlorophenyl)-4-cyanobenzamide (0.39 g), triethylamine (0.51 ml), 4-dimethylaminopyridine (0.01 g) and methylene chloride (25 ml). The mixture was stirred at ambient temperature for 18 hours. The mixture was washed with 2M hydrochloric acid solution and with water. The organic phase was dried ($MgSO_4$)and evaporated. The residue was purified by column chromatography on silica gel using a 49:1 mixture of methylene chloride and methanol as eluent. There was thus obtained the title compound (0.1 1 g);

NMR Spectrum: ($CDCl_3$) 5.5 (s, 2H), 6.58 (d, 1H), 6.7 (d, 1H), 7.18 (d, 1H), 7.93 (s, 8H);

Mass Spectrum: $M-H^-$399;

Elemental Analysis: Found: C, 65.4; H, 3.7; N, 13.1; $C_{22}H_{13}N_4O_2Cl$ $0.25H_2O$ requires C, 65.2; H, 3.4; N, 13.8%.

The N-(3-amino-4-chlorophenyl)-4-cyanobenzamide used as a starting material was prepared as follows:

4-Cyanobenzoyl chloride (11.92 g) was added slowly to a stirred solution of 4-chloro-3-nitroaniline (10.4 g) in pyridine (20 ml) and the mixture was stirred and heated to 115° C. for 18 hours. The mixture was cooled to ambient temperature and poured into water (150 ml) and stirred for 30 minutes. The resultant precipitate was isolated, washed with water and dried to give N-[4-chloro-3-nitrophenyl]-4-cyanobenzamide (18 g), m.p. 213° C.;

NMR Spectrum: ($DMSOd_6$) 7.78 (d, 1H), 8.05 (m, 3H), 8.1 (d, 2H), 8.58 (s, 1H), 10.93 (s, 1H).

A portion (3.6 g) of the material so obtained was added to a stirred suspension of iron powder (10 g) in a mixture of ethanol (130 ml), water (30 ml) and glacial acetic acid (4 ml). The mixture was heated to 75° C. for 1 hour and thereafter, whilst hot, basified by the addition of sodium carbonate. The mixture was filtered and the filtrate was evaporated. The resultant solid was stirred in water for 3 hours. The solid was isolated and dried to give the required starting material (2.7 g), m.p. 237.7° C.; NMR Spectrum: ($DMSOd_6$) 5.44 (s, 2H), 6.98 (m, 1H), 7.21 (d, 1H), 7.42 (d, 1H), 8.07 (d, 2H), 8.14 (d, 2H), 10.36 (s, 1H).

EXAMPLE 6

Using an analogous procedure to that described in Example 5, the appropriate benzoyl chloride was reacted with the appropriate aniline to give the compounds described in Table 11.

TABLE II

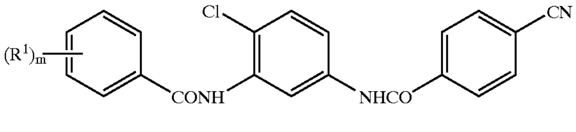

| No. | $(R^1)_m$ | Note | NMR data | Mass |
|---|---|---|---|---|
| 1 | 3,4,5-trimethoxy | | 3.78(s, 3H), 3.88(s, 6H), 7.37(s, 2H), 7.58(d, 1H), 7.72(d, 1H), 8.02(d, 2H), 8.05(s, 1H), 8.10(d, 2H), 10.02(s, 1H), 10.64(s, 1H) | M − H 464 |
| 2 | 3,4-diethoxy | 1. | 1.38(t, 6H), 4.09(m, 4H), 9.83(s, 1H), 10.62(s, 1H) | M − H 462 |
| 3 | 2-hydroxy | | 6.65(t, 1H), 6.9(d, 1H), 7.23(m, 1H), 7.42(d, 1H), 7.62 (m, 1H), 7.93(m, 1H), 7.99(d, 2H), 8.12(d, 2H), 8.98(d, 1H), 10.64(s, 1H) | M + H 392 |
| 4 | 2-hydroxy-4-methoxy | | 3.75(s, 3H), 6.52(s, 1H), 6.61(m, 1H), 7.50(d, 1H), 7.68 (m, 1H), 7.99(m, 3H), 8.1(d, 2H), 8.88(s, 1H), 10.64 (s, 1H), 10.68(s, 1H), 12.2(s, 1H) | M + H 422 |
| 5 | 4-(4-methylpiperazin-1-yl) | | 2.8(s, 3H), 3.4(m, 4H), 4.0(m, 2H), 7.08(d, 2H), 7.52(d, 1H), 7.72(d, 1H), 7.91(d, 2H), 8.0(d, 2H), 8.12(m, 3H), 9.8(s, 1H), 10.68(s, 1H) | M + H 474 |
| 6 | 3-(4-methylpiperazin-1-yl) | | 3.19(s, 3H), 3.5(d, 2H), 3.92(d, 2H), 7.22(d, 1H), 7.41(t, 1H), 7.5(d, 1H), 7.58(t, 1H), 7.72(m, 1H), 8.02(d, 2H), 8.1(m, 2H), 10.06(s, 1H), 10.73(s, 1H) | M + H 474 |

TABLE II-continued

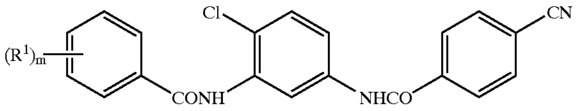

| No. | $(R^1)_m$ | Note | NMR data | Mass |
|---|---|---|---|---|
| 7 | 4-morpholino | | 0.84(m, 2H), 1.29 (m, 2H), 3.23(m, 2H), 3.75(m, 2H), 6.86(m, 1H), 7.01 (d, 1H), 7.13(d, 1H), 7.38(d, 1H), 7.5(d, 1H), 7.7(t, 1H), 7.9(d, 1H), 7.99(d, 2H), 8.05 (d, 2H), 9.68(s, 1H), 10.62(s, 1H) | M + H 461 |

Notes

1. The standard procedure was adapted to the following:
Phosphoryl chloride (0.03 ml) was added dropwise to a stirred mixture of N-(3-amino-4-chlorophenyl)-4-cyanobenzamide (0.08 g), 3,4-diethoxybenzoic acid (0.062 g) and pyridine (4 ml) which had been cooled to −15° C. The mixture was stirred at −15° C. for 3 hours. The mixture was allowed to warm to ambient temperature and was stirred for 16 hours. The mixture was diluted with water and stirred overnight. The resultant precipitate was isolated, washed with diethyl ether and dried under vacuum at 55° C. to give the tabulated compound (0.026 g).

EXAMPLE 7

N-[2-chloro-5-(4-cyanobenzamido)phenyl]-3-fluoro-4-(4-methylpiperazin-1-yl)benzamide Phosphoryl chloride (0.1 I ml) was added dropwise to a stirred mixture of N-(3-amino-4-chlorophenyl)-4-cyanobenzamide (0.2 g), 3-fluoro-4-(4-methylpiperazin-1-yl)benzoic acid (0.26 g) and pyridine (2 ml) which had been cooled to −10° C. The reaction mixture was allowed to warm to ambient temperature and was stirred for 16 hours. The mixture was diluted with water and was stirred overnight. The precipitate was isolated, washed with diethyl ether and dried under vacuum at 55° C. There was thus obtained the title compound as a solid (0.212 g);

Mass Spectrum: $(M-H)^-$ 490.

The 3-fluoro-4-(4-methylpiperazin-1-yl)benzoic acid used as a starting material was obtained as follows:

A mixture of 3,4-difluorobenzonitrile (8.65 g), N-methylpiperazine (7.2 ml), triethylamine (9.1 ml) and acetonitrile (12 ml) was stirred and heated to reflux for 2 hours. The mixture was evaporated and the residue was purified by column chromatography using a 1:5:94 mixture of triethylamine, methanol and methylene chloride as eluent. There was thus obtained 3-fluoro-4-(4-methylpiperazin-1-yl)benzonitrile as an oil which slowly crystallised to give a white solid (12.47 g), m.p. 60–63° C.; NMR Spectrum: ($CDCl_3$) 2.37 (s, 3H), 2.61 (t, 4H), 3.24 (t, 4H), 6.89 (m, 1H), 7.27 (m, 1H), 7.35 (m, 1H).

A portion (3 g) of the material so obtained was dissolved in 6N hydrochloric acid (30 ml) and the solution was heated to reflux for 13 hours. The mixture was cooled to ambient temperature. The precipitate was isolated, washed with water and air-dried to give the required starting material (1.63 g). Elemental analysis showed the crystals to contain approximately 6 equivalents of water. NMR Spectrum: ($DMSOd_6$) 2.81 (s, 3H), 3.28 (m, 8H), 7.17 (m, 1H), 7.62 (m, 1H), 7.71 (m, 1H), 10.9 (s, 1H).

The N-(3-amino-4-chlorophenyl)4-cyanobenzamide used as a starting material was synthesised as follows:

Triethylamine (6.7 ml) was added to a stirred mixture of 3-amino4-chloroaniline (3.44 g), 4-cyanobenzoyl chloride (4.0 g) and methylene chloride (50 ml) which had been cooled to 0° C. The reaction mixture was allowed to warm to ambient temperature and was stirred for 5 hours. The mixture was concentrated to approximately one third of the original volume and a saturated aqueous sodium bicarbonate solution was added. The resultant solid was isolated, washed with water and with methanol and dried under vacuum at 55° C. to give the required starting material (5.23 g); NMR Spectrum: ($DMSOd_6$) 5.37 (s, 2H), 6.9 (m, 1H), 7.14 (d, 1H), 7.35 (d, 1H), 7.98 (d. 2H), 8.08 (d, 2H), 10.28 (s, 1H).

EXAMPLE 8

N-[5-(3-dimethylaminobenzamido)-2-fluorophenyl]-3,4-dimethoxybenzamide 1-(3-Dimethylaminopropyl)-3-ethylcarbodiimide hydrochloride (0.12 g) in methylene chloride (5 ml) was added to a stirred mixture of 3,4-dimethoxybenzoic acid (0.91 g), N-(3-amino-4-fluorophenyl)-3-dimethylaminobenzamide (0.14 g), DMF (2 ml) and 4-dimethylaminopyridine (0.004 g). The reaction mixture was stirred at ambient temperature for 18 hours. Water (20 ml) and methylene chloride (10 ml) were added. The organic phase was washed with a saturated aqueous sodium bicarbonate solution, dried ($MgSO_4$) and evaporated. The residual oil was purified by column chromatography on silica gel using a 49:1 mixture of methylene chloride and methanol as eluent. The material so obtained was triturated under diethyl ether. There was thus obtained the title compound (0.084 g) as a colourles solid, m.p. 187–188° C.; NMR Spectrum: ($CDCl_3$) 3.02 (s, 6H), 3.97 (s, 6H), 6.86 (m, 1H), 6.93 (d, 1H), 7.09 (d, 1H), 7.16 (t, 1H), 7.25 (m, 1H), 7.32 (t, 1H), 7.41 (m, 1 H), 7.5 (d, 1H), 7.88 (m, 1H), 7.97 (s, 1H), 8.04 (s, 1H), 8.42 (m, 1H);

Mass Spectrum: $M+H^+$ 438;

Elemental Analysis: Found C, 65.4; H, 5.5; N, 9.5; $C_{24}H_{24}NFO_4$ requires C, 65.8; H, 5.4; N, 9.6%.

The N-(3-amino4-fluorophenyl)-3-dimethylaminobenzamide used as a starting material was prepared as follows:

Oxalyl chloride (1.2 ml) was added dropwise over 5 minutes to a stirred suspension of 3-dimethylaminobenzoic acid (1.81 g) in methylene chloride (20 ml) at 20° C. DMF (2 drops) was added and the reaction mixture stirred for 4 hours at ambient temperature. The solvent was evaporated and the residue was dissolved in methylene chloride (25 ml) and added over 5 minutes to a stirred mixture of 4-fluoro-3-nitroaniline (1.56 g), triethylamine (4.1 ml) and methylene chloride (25 ml). The solution was stirred for 18 hours. The organic layer was washed with 3M hydrochloric acid and with water, dried ($MgSO_4$) and evaporated. The residual solid was triturated under methyl tert-butyl ether and then under methylene chloride. There was thus obtained N-(4-fluoro-3-nitrophenyl)-3-dimethylaminobenzamide (0.96 g), m.p. 176–177° C.; NMR Spectrum: ($DMSOd_6$) 2.93 (s, 6H), 6.92 (m, 1H), 7.2 (m 2H), 7.31 (t, 1H), 7.56 (q, 1H), 8.11 (m, 1H), 8.63 (m, 1H), 10.58 (s, 1H).

10% Palladium-on-carbon (0.09 g) was added to a stirred suspension of the nitro compound so obtained (0.910 g) in ethanol (90 ml) The mixture was hydrogenated at atmospheric pressure and ambient temperature until hydrogen uptake ceased. The catalyst was removed by filtration and the filtrate was evaporated. The solid residue was purified by column chromatography on silica gel using a 49:1 mixture of methylene chloride and methanol as eluent. There was thus obtained the required starting material (0.74 g);

NMR Spectrum: ($CDCl_3$) 3.0 (s, 6H), 3.78 (s, 2H), 6.7 (m, 1H), 6.92 (m, 2H), 7.05 (d, 1H), 7.30 (m, 2H), 7.37 (m, 1H), 7.68 (s, 1H).

EXAMPLE 9

N-(5-benzamido-2-chlorophenyl)-2-amino-4-methoxybenzamide

Iron powder (2.79 g) was added to a stirred suspension of N-(5-benzamido-2-chlorophenyl)-4-methoxy-2-nitrobenzamide (2.13 g) in a mixture of ethanol (100 ml), water (20 ml) and acetic acid (4 ml). The mixture was stirred and heated to reflux for 6 hours. The mixture was cooled to ambient temperature. Water (50 ml) was added and the resultant mixture was basified by the addition of sodium carbonate. The mixture was filtered and the filtrate was evaporated. The residue was triturated under water. The resultant solid was isolated and dried under vacuum at 40° C. There was thus obtained the title compound (0.911 g);

NMR Spectrum: ($DMSOd_6$) 3.72 (s, 3H), 6.09 (d, 1H), 6.27 (s, 1H), 6.62 (s, 2H), 7.45–7.61 (m, 4H), 7.66–7.72 (m, 2H), 7.95 (d, 2H), 8.07 (s, 1H), 9.52 (s, 1H), 10.37 (s, 1H);

Mass Spectrum: $M+H^+$ 396 and 398.

The N-(5-benzamido-2-chlorophenyl)-4-methoxy-2-nitrobenzamide used as a starting material was prepared as follows:

Benzoyl chloride (5.2 ml) was added to a stirred mixture of 2,4-diaminochlorobenzene (6.42 g), triethylamine (12.5 ml) and methylene chloride (100 ml) which had been cooled to 0° C. The mixture was allowed to warm to ambient temperature and was stirred for 16 hours. The mixture was evaporated and the residue was triturated under a saturated aqueous sodium bicarbonate solution. The resultant solid was isolated, washed in turn with water and isohexane and dried under vacuum at 55° C. There was thus obtained N-(3-amino-4-chlorophenyl)benzamide as a solid (10.38 g); NMR Spectrum: ($DMSOd_6$) 5.32 (s, 2H), 6.9 (m, 1H), 7.1 (d, 1H), 7.37 (d, 1H), 7.52 (m, 3H), 7.9 (d, 2H), 10.05 (s, 1H).

Oxalyl chloride (0.781 ml) was added dropwise to a stirred mixture of 4-methoxy-2-nitrobenzoic acid (1.6 g), DMF (a few drops) and methylene chloride (30 ml) which had been cooled to 0° C. The mixture was allowed to warm to ambient temperature and was stirred for 4 hours. The mixture was evaporated. The residue was dissolved in methylene chloride (10 ml) and added dropwise to a stirred mixture of N-(3-amino-4-chlorophenyl)benzamide (2.0 g), triethylamine (2.49 ml) and methylene chloride (30 ml). The resultant mixture was stirred at ambient temperature for 16 hours. The precipitate was isolated, washed with 1N aqueous hydrochloric acid solution and with methanol and dried under vacuum at 40° C. There was thus obtained the required starting material (2.49 g); NMR Spectrum: ($DMSOd_6$) 3.9 (s, 3H), 7.39 (d, 1H), 7.47–7.62 (m, 5H), 7.72 (d, 1H), 7.78 (d, 1H), 7.97 (d, 2H), 8.14 (s, 1H), 10.28 (s, 1H), 10.46 (s, 1H);. Mass Spectrum: $M+H^+$ 426 and 428.

EXAMPLE 10

N-(5-benzamido-2-chlorophenyl)-3,4dimethoxybenzamide

Phosphoryl chloride (0.074 g) was added to a stirred mixture of 3,4-dimethoxybenzoic acid (0.088 g), N-(3-amino-4-chlorophenyl)benzamide (0.1 g) and pyridine (1 ml) which had been cooled to 0° C. The mixture was allowed to warm to ambient temperature and was stirred for 16 hours. The mixture was poured into 1N aqueous hydrochloric acid solution and the resultant solid was isolated, washed with a saturated aqueous sodium bicarbonate solution and dried under vacuum at 55° C. There was thus obtained the title compound (0.088 g);

NMR Spectrum: ($DMSOd_6$) 3.83 (m, 6H), 7.09 (d, 1H), 7.55 (m, 6H), 7.72 (d, 1H), 7.95 (d, 2H), 8.08 (s, 1H), 9.88 (s, 1H), 10.4 (s, 1H);

Mass Spectrum: $M-H^-$409.

EXAMPLE 11

N-[2-chloro-5-(2-nitrobenzamido)phenyl]-3,4-dimethoxybenzamide 3,4-Dimethoxybenzoyl chloride (1.55 g) was added to a stirred mixture of N-(3-amino-4-chlorophenyl)-2-nitrobenzamide (1.5 g) and pyridine (20 ml) and the mixture was stirred and heated to 80° C. for 16 hours. The mixture was cooled to ambient temperature and evaporated. The residue was partitioned between methylene chloride and 1N aqueous hydrochloric acid solution. The organic phase was washed with a saturated aqueous sodium bicarbonate solution and evaporated. The residue was triturated under ethyl acetate. The resultant solid was isolated, washed with a saturated aqueous sodium bicarbonate solution and dried under vacuum at 40° C. There was thus obtained the title compound (1.63 g);

NMR Spectrum: ($DMSOd_6$) 7.08 (d, 1H), 7.52–7.57 (m, 3H), 7.62 (d, 1H), 7.74–7.8 (m, 2H), 7.86 (t, 1H), 7.87 (s, 1H), 8.13 (d, 1H);

Mass Spectrum: $M+H^+$ 456 and 458.

The N-(3-amino-4-chlorophenyl)-2-nitrobenzamide used as a starting material was prepared as follows:

2-Nitrobenzoyl chloride (4.64 ml) was added to a stirred mixture of 3-amino-4-chloroaniline (5 g), triethylamine (9.78 ml) and methylene chloride (300 ml) and the reaction mixture was stirred at ambient temperature for 16 hours. The mixture was partitioned between methylene chloride and a saturated aqueous sodium bicarbonate solution. The organic phase was evaporated and the residue was purified by column chromatography on silica to give the required starting material (3.02 g); NMR Spectrum: ($DMSOd_6$) 5.38 (s, 2H), 6.74 (d, 1H), 7.11 (d, 1H), 7.27 (s, 1H), 7.7–7.75 (m, 2H), 7.84 (t, 1H), 8.1 (d, 1H), 10.5 (s, 1H); Mass Spectrum: $M+H^+$ 292 and 294.

EXAMPLE 12

N-15-(2-aminobenzamido)-2-chlorophenyl]-3,4-dimethoxybenzamide

Using an analogous procedure to that described in Example 9, N-[2-chloro-5-(2-nitrobenzamido)phenyl]-3,4-dimethoxybenzamide was reduced by iron powder in the presence of acetic acid to give the title compound in 43% yield;

NMR Spectrum: ($DMSOd_6$) 3.82 (s, 6H), 6.32 (s, 2H), 6.58 (t, 1H), 7.74 (d, 1H), 7.08 (d, 1H), 7.19 (t, 1H), 7.47 (d, 1H), 7.52–7.64 (m, 4H), 8.04 (s, 1H), 9.88 (s, 1H), 10.13 (s, 1H);

Mass Spectrum: $M+H^+$ 426.

EXAMPLE 13

N-[2-chloro-5-(3-dimethylaminobenzamido)4-fluorophenyl]-3,4-dimethoxybenzamide A mixture of 3,4-dimethoxybenzoyl chloride (0.5 g), N-(5-amino-4-chloro-2-fluorophenyl)-3-dimethylaminobenzamide (0.781 g) and pyridine (8 ml) was stirred at ambient temperature for 18 hours. The mixture was evaporated and the residue was partitioned between methylene chloride and a saturated aqueous copper sulphate solution. The organic phase was washed in turn with water and a saturated aqueous sodium chloride solution, dried ($MgSO_4$) and evaporated. The residue was purified by column chromatography on silica using a 99:1 mixture of methylene chloride and methanol as eluent. There was thus obtained the title compound as a solid (0.328 g);

NMR Spectrurn: ($CDCl_3$) 3.02 (s, 6H), 3.98 (s, 6H), 6.96 (m, 2H), 7.06 (m, 1H), 7.06–7.47 (m, 3H), 7.47 (m, 1H), 7.6 (m, 1H), 8.01 (s, 1H), 8.2 (s, 1H), 9.53 (m, 1H);

Mass Spectrum: $M+H^+$ 472 and 474.

The N-(5-amino4-chloro-2-fluorophenyl)-3-dimethylaminobenzamide used as a starting material was prepared as follows:

Phthalic anhydride (11.83 g) was added to a solution of 2-chloro4-fluoroaniline (11.08 g) in glacial acetic acid (150 ml) and the mixture was stirred and heated to 100° C. for 2 hours. The mixture was allowed to cool to ambient temperature and the precipitate was isolated, washed with water and dried under vacuum. There was thus obtained N-(2-chloro-4-fluorophenyl)phthalimide which was used without further purification.

A mixture of nitric acid (4.6 ml) and sulphuric acid (5 ml) was added gradually to a stirred mixture of the N-(2-chloro-4-fluorophenyl)phthalimide so obtained and sulphuric acid (30 ml) which was cooled in an ice-water bath, the rate of addition was such that the internal reaction temperature did not exceed 30° C. The resulting clear solution was stirred at ambient temperature for 1 hour. A mixture (250 ml) of ice and water was added and the precipitated solid was isolated and dried under vacuum. There was thus obtained N-(2-chloro-4-fluoro-5-nitrophenyl)phthalimide as a solid (17.9 g); NMR Spectrum: ($CDCl_3$): 7.58 (d, 1H), 7.88 (m, 2H), 8.01 (m, 2H), 8.16 (d, 1H); Mass Spectrum: $M-H^-$ 319 and 321.

A mixture of ethanol (450 ml), water (65 ml) and acetic acid (6.5 ml) was stirred and heated to 50° C. Iron powder (9 g) was added followed by portionwise addition over 10 minutes of N-(2-chloro-4-fluoro-5-nitrophenyl)phthalimide (8.98 g). The resultant mixture was stirred and heated to reflux for 2 hours. The mixture was cooled to ambient temperature and basified by the addition of solid sodium carbonate. The mixture was filtered and the filtrate was evaporated. The residue was partitioned between methylene chloride and a saturated aqueous sodium bicarbonate solution. The organic extract was washed with a saturated aqueous sodium chloride solution, dried over sodium sulphate and evaporated. There was thus obtained N-(5-amino-2-chloro-4-fluorophenyl)phthalimide as a solid (6.3 g);

NMR Spectrum: ($CDCl_3$) 3.87 (s, 2H), 6.74 (d. 1H), 7.2 (d. 1H), 7.81 (m, 2H), 7.96 (m, 2H);

Mass Spectrum: $M-H^-$ 289 and 291.

Pyridine (2.0 ml) was added to a mixture of N-(5-amino-2-chloro-4-fluorophenyl)phthalimide (2.9 g), 3-dimethylaminobenzoyl chloride hydrochloride (3.06 g) and methylene chloride (20 ml) and the mixture was stirred at ambient temperature for 18 hours. The reaction mixture was diluted with methylene chloride (200 ml) and washed in turn with a saturated aqueous copper sulphate solution and water. The organic solution was dried ($MgSO_4$) and evaporated. The residue was triturated under ethyl acetate. The solid so obtained was isolated and washed with ethyl acetate and with diethyl ether. There was thus obtained N-(4-chloro- 2-fluoro-5-phthalimidophenyl)-3-dimethylaminobenzamide as a solid (2.46 g); NMR Spectrum: ($DMSOd_6$) 2.94 (s, 6H), 6.94 (m, 1H), 7.28 (m, 3H), 7.8–7.92 (m, 2H), 7.94 (m, 2H), 8.02 (m, 2H); Mass Spectrum: $M+H^+$ 438 and 440.

A mixture of the material so obtained, ethanolamine (0.68 ml) and methylene chloride (40 ml) was stirred at ambient temperature for 4 hours. The mixture was diluted with methylene chloride (200 ml) and the resultant solution was washed with water and with a saturated aqueous sodium chloride solution, dried over sodium sulphate and evaporated. There was thus obtained N-(5-amino-4-chloro-2-fluorophenyl)-3-dimethylaminobenzamide as a solid (1.26 g); NMR Spectrum: ($CDCl_3$) 3.02 (s, 6H), 3.94 (s, 2H), 4.0 (broad s, 2H), 6.88 (m, 1H), 7.04 (m, 1H), 7.07 (s, 1H), 7.25 (m, 1H), 7.32 (t, 1H), 7.98 (broad s, 1H), 8.08 (d, 1H); Mass Spectrum: $M+H^+$ 308 and 310.

EXAMPLE 14

N-[5-(4-acetoxybenzamido)-2-chlorophenyl]-4-cyanobenzamide

Oxalyl chloride (0.35 ml) was added to a stirred suspension of 4-acetoxybenzoic acid (0.57 g) in methylene chloride (15 ml) which had been cooled to 0° C. DMF (2 drops) was added and the mixture was stirred at ambient temperature for 4 hours. The mixture was evaporated to give 4-acetoxybenzoyl chloride which was used without further purification. A mixture of the acid chloride so obtained, N-(3-amino-4-chlorophenyl)-4-cyanobenzamide (0.813 g) and pyridine (15 ml) was stirred and heated at 100° C. for 16 hours. The mixture was cooled to ambient temperature and poured into 2N aqueous hydrochloric acid solution (175 ml). The precipitate was isolated, washed with water and dried. The material so obtained was purified by column chromatography on silica using a 7:3 mixture of isohexane and ethyl acetate as eluent. There was thus obtained the title compound (0.74 g); m.p. 195–196° C.

NMR Spectumn: ($DMSOd_6$) 2.3 (s, 3H), 7.28 (d, 2H), 7.51 (d, 1H), 7.73 (m, 1H), 7.81 (m, 4H), 8.12 (m, 3H), 10.08 (s, 1H), 10.64 (s, 1H);

Mass Spectrum: $M+H^+$ 434.

EXAMPLE 15

N-[2-chloro-5-(3-morpholinobenzamido)phenyl]-4-cyanobenzamide

Using an analogous procedure to that described in Example 14, 3-morpholinobenzoyl chloride was reacted with N-(3-amino-4-chlorophenyl)-4-cyanobenzamide to give the title compound in 42% yield;

NMR Spectrum: ($DMSOd_6$) 3.13 (t, 4H), 3.73 (t, 4H), 7.17 (s, 1H), 7.43 (m, 1H), 7.6 (d, 1H), 7.8 (m, 1H), 8.06 (m, 3H), 8.1 (m, 3H), 8.17 (m, 1H);

Mass Spectrum: $M+H^+$ 461.

EXAMPLE 16

Pharmaceutical Compositions

The following illustrate representative pharmaceutical dosage forms of the invention as defined herein (the active ingredient being termed "Compound X"), for therapeutic or prophylactic use in humans:

| | mg/tablet |
|---|---|
| (a) Tablet I | |
| Compound X | 100 |
| Lactose Ph. Eur | 182.75 |
| Croscarmellose sodium | 12.0 |
| Maize starch paste (5% W/V paste) | 2.25 |
| Magnesium stearate 3.0 | |

| | mg/tablet |
|---|---|
| (b) Tablet II | |
| Compound X | 50 |
| Lactose Ph. Eur | 223.75 |
| Croscamellose sodium | 6.0 |
| Maize starch | 15.0 |
| Polyvinylpyrrolidone (5% W/V paste) | 2.25 |
| Magnesium stearate | 3.0 |

| | mg/tablet |
|---|---|
| (c) Tablet III | |
| Compound X | 1.0 |
| Lactose Ph. Eur | 93.25 |
| Croscamellose sodium | 4.0 |
| Maize starch paste (5% W/V paste) | 0.75 |
| Magnesium stearate | 1.0 |

| | mg/capsule |
|---|---|
| (d) Capsule | |
| Compound X | 10 |
| Lactose Ph. Eur | 488.5 |
| Magnesium | 1.5 |

| | (50 ml/mg) |
|---|---|
| (e) Injection 1 | |
| Compound X | 5.0% w/v |
| 1M Sodium hydroxide solution | 15.0% v/v |
| 0.1M Hydrochloric acid (to adjust pH to 7.6) | |
| Polyetbylene glycol 400 | 4.5% w/v |
| Water for injection to 100% | |

| | (10 mg/ml) |
|---|---|
| (f) Injection II | |
| Compound X | 1.0% w/v |
| Sodium phosphate BP | 3.6% w/v |
| 0.1M Sodium hydroxide solution | 15.0% v/v |
| Water for injection to 100% | |

| | (1 mg/ml, buffered to pH 6) |
|---|---|
| (g) Injection III | |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| | mg/ml |
|---|---|
| (h) Aerosol I | |
| Compound X | 10.0 |
| Sorbitan trioleate | 13.5 |
| Trichlorofluoromethane | 910.0 |
| Dichlorodifluoromethane | 490.0 |

| | mg/ml |
|---|---|

-continued

| | |
|---|---|
| (i) Aerosol II | |
| Compound X | 0.2 |
| Sorbitan trioleate | 0.27 |
| Trichlorofluoromethane | 70.0 |
| Dichiorodifluoromethane | 280.0 |
| Dichlorotetrafluoroethane | 1094.0 |
| | mg/ml |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| | mg/ml |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |
| | ml |
| (l) Ointment | |
| Compound X | 40 mg |
| Ethanol | 300 μl |
| Water | 300 μl |
| 1-Dodecylazacycloheptan-2-one | 50 μl |
| Propylene glycol | to 1 ml |

Note
The above fonnulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of the Formula I

Formula I

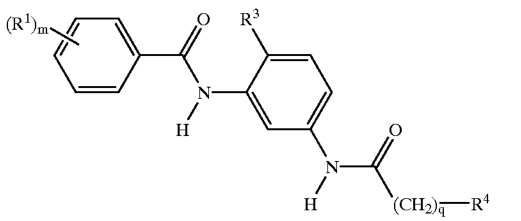

wherein:

$R^1$ is selected from hydroxy, $C_{1-6}$alkoxy, mercapto, $C_{1-6}$alkylthio, amino, $C_{1-6}$alkylamino, di-($C_{1-6}$alkyl) amino, carboxy, $C_{1-6}$alkoxycarbonyl, carbamoyl, $C_{1-6}$alkylcarbamoyl, di-$C_{1-6}$alkylcarbamoyl, $C_{1-6}$alkylsulphinyl, $C_{1-6}$alkylsulphonyl, arylsulphinyl, arylsulphonyl, $C_{1-6}$alkylaminosulphonyl, di-($C_{1-6}$alkyl)aminosulphonyl, nitro, cyano, cyano$C_{1-6}$alkyl, hydroxy$C_{1-6}$alkyl, amino$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, $C_{2-6}$alkenyl, $C_{2-6}$alkynyl, halo, trifluoromethyl, aryl, aryl$C_{1-6}$alkyl, aryl$C_{1-6}$alkoxy, heteroaryl, heteroaryl$C_{1-6}$alkyl, heterocyclyl or heterocyclyl$C_{1-6}$alkyl;

m is 1 or 2 and when m is 2 each $R^1$ group may be the same or different;

$R^3$ is halo;

q is 0–4; and $R^4$ is aryl or cycloalkyl wherein $R^4$ is optionally substituted with up to 3 substituents having any value defined for each $R^1$ group;

or a pharmaceutically-acceptable salt or in-vivo-cleavable ester thereof; with the proviso that:

N-[2-bromo-5-(3-cyclohexylpropionylamino)phenyl]-4-hydroxybenzamide,

N-[2-chloro-5-(3 -cyclohexylpropionylamino)phenyl]-4-acetoxybenzamide,

N-[2-chloro-5-(3-cyclohexylpropionylamino)phenyl]-4-hydroxybenzamide and

N-[2-fluoro-5-(3-cyclohexylpropionylamino)phenyl]-4-hydroxybenzamide are excluded.

2. A compound of the Formula I according to claim 1, wherein $R^1$ is hydroxy, methoxy, ethoxy, propoxy, isopropoxy, butoxy, amino, methylamino, ethylamino, dimethylamino, diethylamino, carboxy, methoxycarbonyl, ethoxycarbonyl, tert-butoxycarbonyl, cyano, acetamido, acetyl, acetoxy, methyl, ethyl, propyl, isopropyl, butyl, tert-butyl, fluoro, chloro, trifluoromethyl, pyrrolidin-1-yl, morpholino, piperidino, piperazin-1-yl or 4-methylpiperazin-1-yl;

$R^3$ is fluoro, chloro or bromo;

q is 1, 2 or 3; and $R^4$ is cyclohexyl or cyclopentyl;

or a pharmaceutically-acceptable salt thereof.

3. A compound of the Formula I according to claim 1, wherein $R^1$ is hydroxy, methoxy, ethoxy, propoxy, isopropoxy, butoxy, amino, methylamino, ethylamino, dimethylamino, diethylamino, carboxy, methoxycarbonyl, ethoxycarbonyl, tert-butoxycarbonyl, cyano, acetamido, acetyl, acetoxy, methyl, ethyl, propyl, isopropyl, butyl, tert-butyl, fluoro, chloro, trifluoromethyl, pyrrolidin-1-yl, morpholino, piperidino, piperazin-1-yl or 4-methylpiperazin-1-yl;

$R^3$ is fluoro, chloro or bromo;

q is 0; and $R^4$ is phenyl which is optionally substituted with 1 or 2 substituents selected from hydroxy, methoxy, ethoxy, propoxy, amino, methylamino, ethylamino, propylamino, dimethylamino, diethylamino, carboxy, methoxycarbonyl, ethoxycarbonyl, nitro, cyano, acetamido, acetyl, acetoxy, methyl, ethyl, fluoro, chloro, bromo, trifluoromethyl, phenyl, benzyloxy, pyrrolidin-1-yl, morpholino, piperidino, piperazin-1-yl or 4-methylpiperazin-1-yl;

or a pharmaceutically-acceptable salt thereof.

4. A compound of the Formula I according to claim 1, wherein $R^1$ is hydroxy, methoxy, ethoxy, cyano, fluoro, chloro, morpholino or 4-methylpiperazin-1-yl;

$R^3$ is fluoro, chloro or bromo;

q is 0; and $R^4$ is phenyl which is substituted with 1 or 2 substituents selected from hydroxy, methoxy, dimethylamino, methoxycarbonyl, cyano, fluoro, chloro and morpholino;

or a pharmaceutically-acceptable salt thereof.

5. A compound of the Formula I according to claim 1, wherein $R^1$ is hydroxy, methoxy, ethoxy, amino, cyano, acetoxy, fluoro, chloro, morpholino or 4-methylpiperazin-1-yl;

$R^3$ is fluoro, chloro or bromo;

q is 0; and $R^4$ is phenyl which is unsubstituted or substituted with 1 or 2 substituents selected from hydroxy, methoxy, amino, dimethylamino, methoxycarbonyl, nitro, cyano, fluoro, chloro and morpholino;

or a pharmaceutically-acceptable salt thereof.

6. A compound of the Formula I according to claim 1, selected from:

N-[2-chloro-5-(3-cyanobenzamido)phenyl]-3,4-dimethoxybenzamide,

N-[2-chloro-5-(3-dimethylaminobenzamido)phenyl]-3,4-dimethoxybenzamide,

N-[2-chloro-5-(4-cyanobenzamido)phenyl]-3,4-dimethoxybenzamide and

N-[2-chloro-5-(4-cyanobenzamido)phenyl]-3-(4-methylpiperazin-1-yl)benzamide;

or pharmaceutically-acceptable salts thereof.

7. A compound of the Formula I according to claim 1, selected from:

N-(5-benzamido-2-chlorophenyl)-3,4-dimethoxybenzamide,

N-[2-chloro-5-(3-morpholinobenzamido)phenyl]-3,4-dimethoxybenzamide,

N-[5-(4-acetoxybenzamido)-2-chlorophenyl]-4-cyanobenzamide,

N-(5-benzamido-2-chlorophenyl)-2-amino-4-methoxybenzamide and

N-[2-chloro-5-(3-morpholinobenzamido)phenyl]-4-cyanobenzamide;

or pharmaceutically-acceptable salts thereof.

8. A process for the preparation of a compound of the Formula I, or a pharmaceutically-acceptable salt or in-vivo-cleavable ester thereof, according to claim 1 which comprises:

(a) reacting of a compound of the Formula II

Formula II

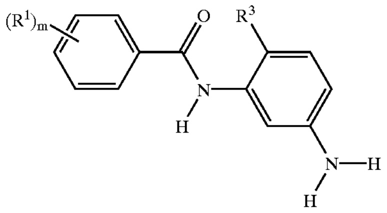

with an acid of the Formula III

Formula III

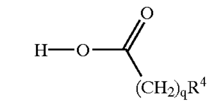

or an activated derivative thereof, under standard amide bond forming conditions, wherein variable groups are as defined in claim 1 and wherein any functional group is protected if necessary, and:

(i) removing any protecting groups;

(ii) optionally forming a pharmaceutically-acceptable salt or in-vivo-cleavable ester;

(b) reacting of an acid of the Formula V

Formula V

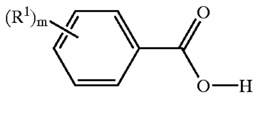

or an activated derivative thereof, with an aniline of the Formula VII

Formula VII

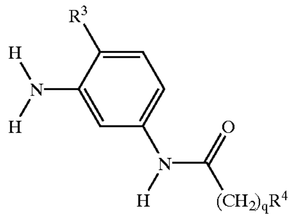

under standard amide bond forming conditions, wherein variable groups are as defined in claim 1 and wherein any functional group is protected, if necessary, and:

(i) removing any protecting groups;

(ii) optionally forming a pharmaceutically-acceptable salt or in-vivo-cleavable ester; or (c) for the preparation of a compound of the Formula I according to claim 1 wherein $R^1$ a substituent on $R^4$ is an amino group, reducing of a compound of the Formula I wherein $R^1$ or a substituent on $R^4$ is a nitro group.

9. A pharmaceutical composition which comprises a compound of the Formula I, or a pharmaceutically-acceptable salt or in-vivo-cleavable ester thereof, according to claim 1 in association with a pharmaceutically-acceptable diluent or carrier.

10. A method of treating a disease or medical condition mediated by cytokines which comprises administering to a warm-blooded animal an effective amount of a compound of the Formula I, or a pharmaceutically-acceptable salt or in-vivo-cleavable ester thereof, according to claim 1.

* * * * *